United States Patent [19]

Uster et al.

[11] Patent Number: 4,828,837
[45] Date of Patent: May 9, 1989

[54] NON-CRYSTALLINE MINOXIDIL COMPOSITION, ITS PRODUCTION AND APPLICATION

[75] Inventors: Paul S. Uster, Palo Alto; Yolanda P. Quinn, Daly City, both of Calif.

[73] Assignee: Liposome Technology, Inc., Menlo Park, Calif.

[21] Appl. No.: 32,512

[22] Filed: Mar. 30, 1987

[51] Int. Cl.$^4$ .................. A61K 37/22; A61K 9/66; B01J 13/02

[52] U.S. Cl. .................. 424/450; 264/4.1; 264/4.6; 424/1.1; 424/45; 424/449; 428/402.2; 436/829; 514/78; 514/944; 514/947; 514/969

[58] Field of Search .................. 264/4.1; 428/402.2; 424/45, 450; 436/829; 514/78, 947, 969

[56] References Cited

U.S. PATENT DOCUMENTS 4,654,354  3/1987  Shroot et al. .................. 514/373 X
4,670,185  6/1987  Fujiwara et al. .................. 264/4.1 X

FOREIGN PATENT DOCUMENTS 0161445  11/1985  European Pat. Off. .............. 514/78
0177223  4/1986  European Pat. Off. .
2145107  3/1985  United Kingdom .................. 424/45

Primary Examiner—Richard D. Lovering
Attorney, Agent, or Firm—Dressler, Goldsmith, Shore, Sutker & Milnamow

[57] ABSTRACT

An aqueous, noncrystalline minoxidil composition for topical use. The composition contains minoxidil complexed with an amphipathic compound having a pK less than about 5 and containing a single lipophilic chain moiety and a sulfate, sulfonate, phosphate and phosphonate polar moiety. The composition may be formulated in ointment form, in an aqueous vehicle, or dispersed in a fluorochlorocarbon solvent, for spray delivery from a self-propelled spray device.

18 Claims, 11 Drawing Sheets

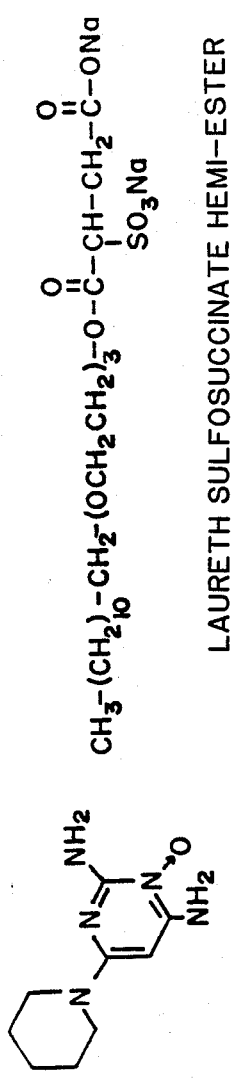
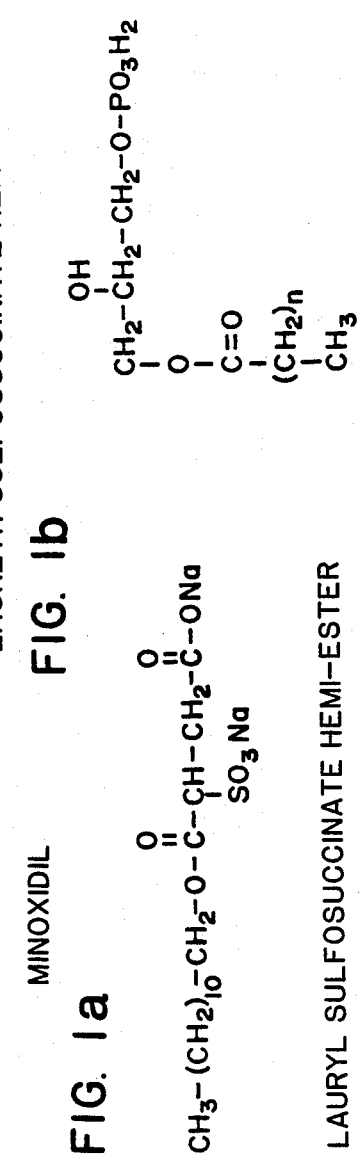
FIG. 1a MINOXIDIL
FIG. 1b LAURETH SULFOSUCCINATE HEMI-ESTER
FIG. 1c LAURYL SULFOSUCCINATE HEMI-ESTER
FIG. 1d LYSO PHOSPHATIDIC ACID $CH_3-(CH_2)_7-CH=CH(CH_2)_7-CH_2(OCH_2CH_2)_3-OPO_3H_2$

CRODAFO3 N3 ACID (OLETH 3 PHOSPHORIC ACID)

FIG. 1e $CH_3(CH_2)_n-PO_3Na_2$

ALKYL PHOSPHONATE

FIG. 1f $CH_3-(CH_3)_n-SO_3Na$

ALKYL SULFONATE

FIG. 1h $CH_3(CH_2)_n-OSO_3Na$

ALKYL SULFATE ESTER

FIG. 1g $$CH_3(CH_2)_7-CH=CH(CH_2)_7-\underset{\underset{SO_3Na}{|}}{\overset{\overset{NH}{|}}{C}}=O$$
$$NaO-\overset{O}{\underset{}{C}}-CH_2-CH-\overset{O}{\underset{}{C}}-(OCH_2CH_2)_3$$

OLEAMIDO POLYETHYLENE
GLYCOL-Z SULFOSUCCINATE
HEMI-ESTER

FIG. 1i

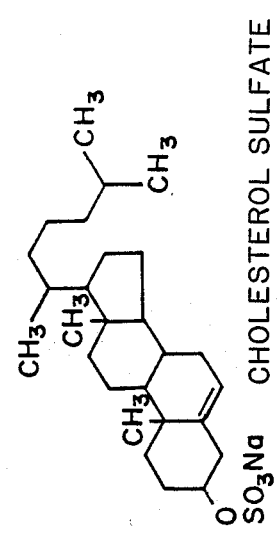
FIG. 2b CHOLESTEROL SULFATE
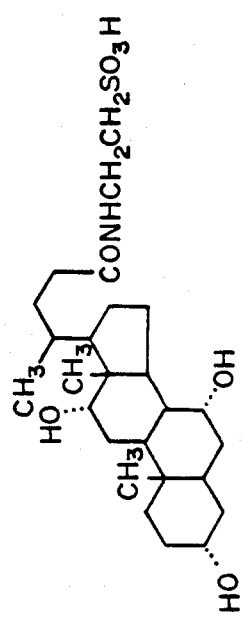
FIG. 2a TAUROCHOLIC ACID

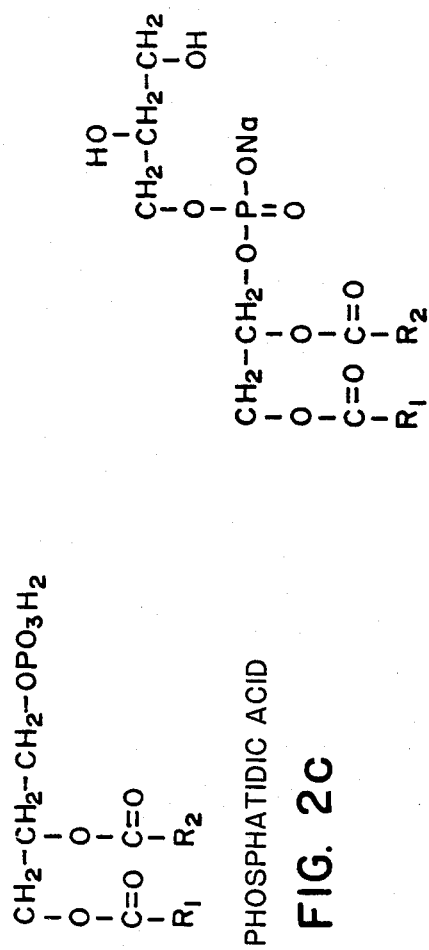
FIG. 2c — PHOSPHATIDIC ACID
FIG. 2d — PHOSPHATIDYLGLYCEROL
WHERE $R_1$ AND $R_2$ REPRESENT ANY FATTY ACID

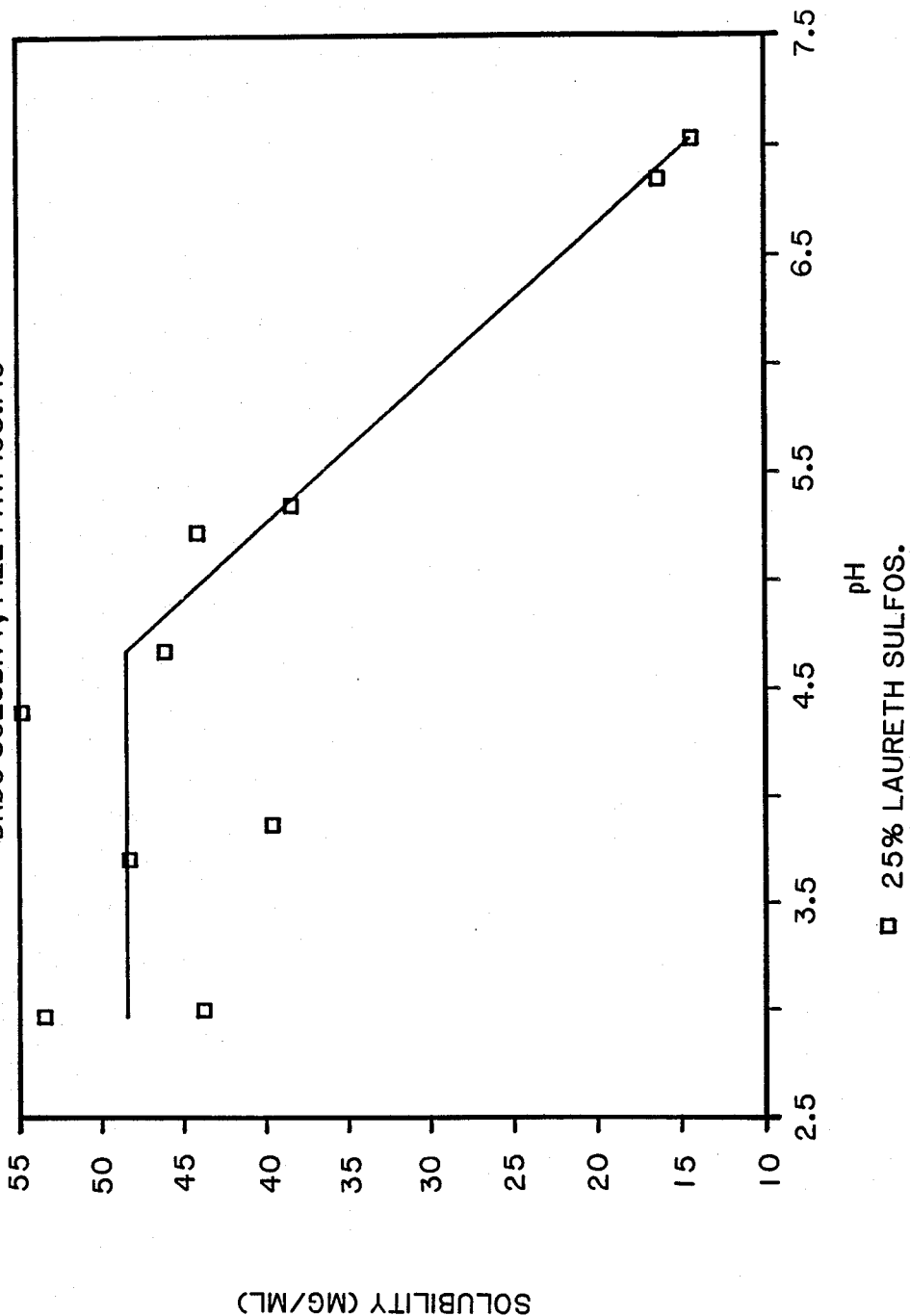

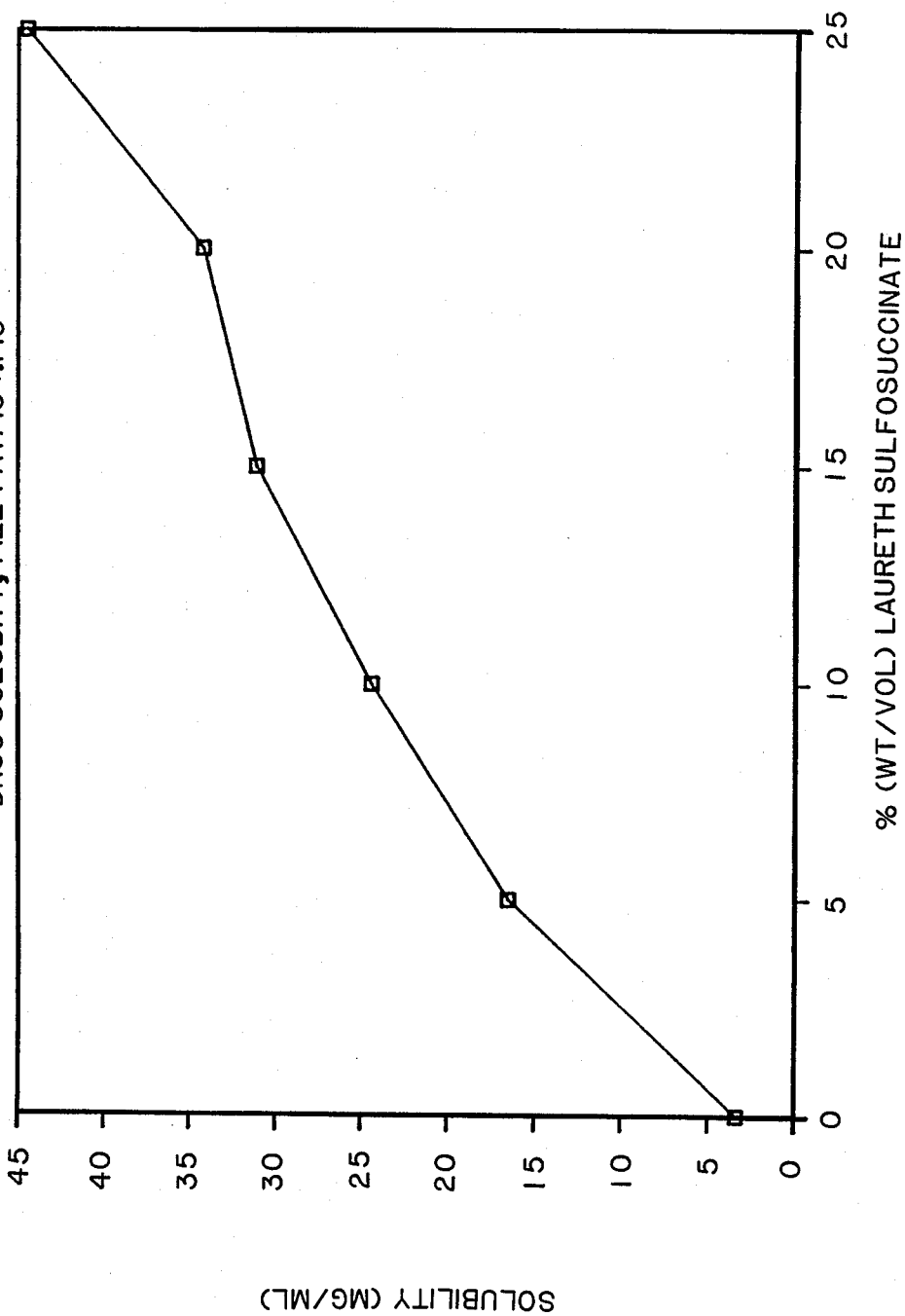

NON-CRYSTALLINE MINOXIDIL COMPOSITION, ITS PRODUCTION AND APPLICATION

FIELD OF THE INVENTION

The present invention relates to a topical minoxidil composition, and in particular, to a non-crystalline composition which can be applied in spray or ointment form.

BACKGROUND OF THE INVENTION

Minoxidil is an arterial dilator which has been used, in oral form, in the treatment of hypertension to lower blood pressure. More recently, the drug has been shown to stimulate new hair growth, when applied topically, in cases of male pattern baldness. Initial clinical studies with a topical form of the drug indicate that reversal of male pattern baldness is most favorable in younger men, and where recent hair loss has occurred, but that new hair growth is observed in a significant percentage of older men and/or in cases of long-term baldness.

The drug itself is a piperidinyl pyrimidine compound which is poorly soluble in water and in most water-immiscible organic solvents such as chloroform. Heretofore, minoxidil has been formulated, for topical use, in an ethanol-based ointment vehicle containing ethanol, propylene glycol and water. The solubility of the drug in pure propylene glycol is between about 7-9% by weight, and in an ethanol/propylene glycol/water vehicle, only about 2%. One drawback of the formulation is the tendency of the minoxidil to revert to an insoluble crystalline form when applied to the skin, as the ethanol solvent evaporates. Whether due to the tendency of the drug to crystallize or other factors, the minoxidil formulation shows relatively inefficient uptake by the skin. Another limitation is the limited solubility of the drug in the ethanol/propylene glycol/water vehicle. Further, evaporation of ethanol, when the formulation is applied to the skin, leaves a viscous propylene glycol/water residue which may be objectionable to many users. The drug is poorly soluble in water and practically insoluble in lipophilic solvents, such as chloroform. Therefore, predominantly water-based or propellant-solvent formulations have not been feasible heretofore.

European patent application No. 177,223 discloses a liposomal minoxidil composition in which minoxidil is present (1) in solution form possibly in a supersaturated state, either encapsulated in lipid vesicles, or in the aqueous or lipid phases of a liposome suspension, and (2) in a finely divided crystalline (solid) form both within and outside the lipid vesicles. Preferred embodiments of the composition are formed by hydrating a minoxidil lipid film containing a saturated phosphatidylcholine (PC), such as dipalmitoylphosphatidylcholine (DPPC), cholesterol, and minoxidil with an aqueous solution containing minoxidil in ethanol/propylene glycol and water. Minoxidil is present at a final weight concentration of between about 1.2-3%. The composition was found to contain liposomes of various sizes between about $1\mu$ to $15\mu$, and minoxidil crystals. Although the formulation is reported to increase drug uptake by the epidermis when applied topically to skin, it has the same limitation as the above non-liposomal formulation in that the drug is applied to the skin largely in crystalline form.

SUMMARY OF THE INVENTION

It is one general object of the present invention to provide a non-crystalline minoxidil composition that can be formulated in a water-based or lipophilic-solvent vehicle.

Another object of the invention is to provide such a formulation which gives enhanced transdermal penetration of the drug.

The invention includes a non-crystalline minoxidil composition in which minoxidil is complexed with an amphipathic compound having a pK of less than about 5, and containing a single lipophilic chain and a polar head moiety selected from a sulfate, sulfonate, phosphate, or phosphonate free acid. The molar ratio of the amphipath to minoxidil is at least about 1:1, and the composition has a preferred pH between about 4-6. Preferred amphipathic compounds include sulfosuccinic acid hemiesters and alkyl phosphonates and phosphate esters, and exemplary sulfosuccinic acid hemiesters include ethoxylated sulfosuccinic acid hemiesters, such as the free acids or laureth, lauryl or oleamidopolyethylene glycol sulfosuccinate.

The composition may further include vesicle-forming lipids, such as PC, at a preferred molar ratio of lipid to minoxidil of between about 1:1 to 4:1.

The minoxidil composition may be administered in either spray or ointment form. A convenient spray formulation includes the minoxidil/ester complex dispersed in a chlorofluorocarbon propellant solvent. Phospholipid, such as PC, may be added to achieve a molecular monodisperse form of the drug in the solvent. The minoxidil spray is directed against the topical area of interest, to deposit (with solvent evaporation) a non-crystalline minoxidil composition on the skin.

In a cream or ointment formulation, the minoxidil composition is dispersed in non-crystalline form in an aqueous medium, in the presence or absence of suspended liposomal or lipid-emulsion particles. The formulation typically contains 1-6% minoxidil, at least an equal molar amount of the amphipathic compound, and between about 60-90% water. In a liposomal formulation, the vesicle-forming lipids are present at a weight ratio of lipids to minoxidil of between about 1:1 and 4:1, where the transdermal uptake of minoxidil is reduced at higher lipid to drug ratios.

More generally, this composition includes a non-crystalline minoxidil composition in which minoxidil is (a) present at a weight concentration of between about 1-6%; (b) complexed with an amphipathic compound having a pK less than about 5, at an amphipath:minoxidil molar ratio of at least about 1:1; (c) dispersed in an aqueous or lipophilic-solvent carrier, and (d) maintained in non-crystalline form for a period of at least several hours after application to the skin. The amphipathic compound is preferably one which promotes transdermal uptake of the drug.

Also forming part of the invention is a method for applying minoxidil topically in a substantially noncrystalline form which remains in non-crystalline form at least several hours after application to the skin. The method includes complexing the minoxidil with an amphipathic compound having a pK less than about 5, and containing a single lipophilic chain moiety and a polar head moiety selected from a sulfate, sulfonate, phosphate, or phosphonate free acid. Specific formulations, and methods of application of the complex to the skin are as described above.

These and other objects and features of the invention will become more fully apparent when the following detailed description of the invention is read in conjunction with the accompanying drawings.

BRIEF DESCRIPTION OF THE DRAWINGS

FIG. 1 shows the molecular structure of minoxidil (1a) and the structures of several amphipathic compounds which promote solubilization of minoxidil in aqueous and lipophilic solvents and lipid bodies, and enhance transdermal uptake of the drug (1b-1i);

FIG. 2 shows the molecular structures of several amphipathic compounds (2a-2d) which promote solubilization of minoxidil uptake, but do not enhance skin penetration of the drug;

FIG. 3 is a plot showing changes in minoxidil solubility, in a 20% laureth sulfosuccinate mixture, as a function of pH;

FIG. 4 is a plot showing the increase in minoxidil solubility with increased concentrations of laureth sulfosuccinate in a pH 5.0 mixture;

DETAILED DESCRIPTION OF THE INVENTION

I. Minoxidil Composition in Aqueous Medium

Figure 5:
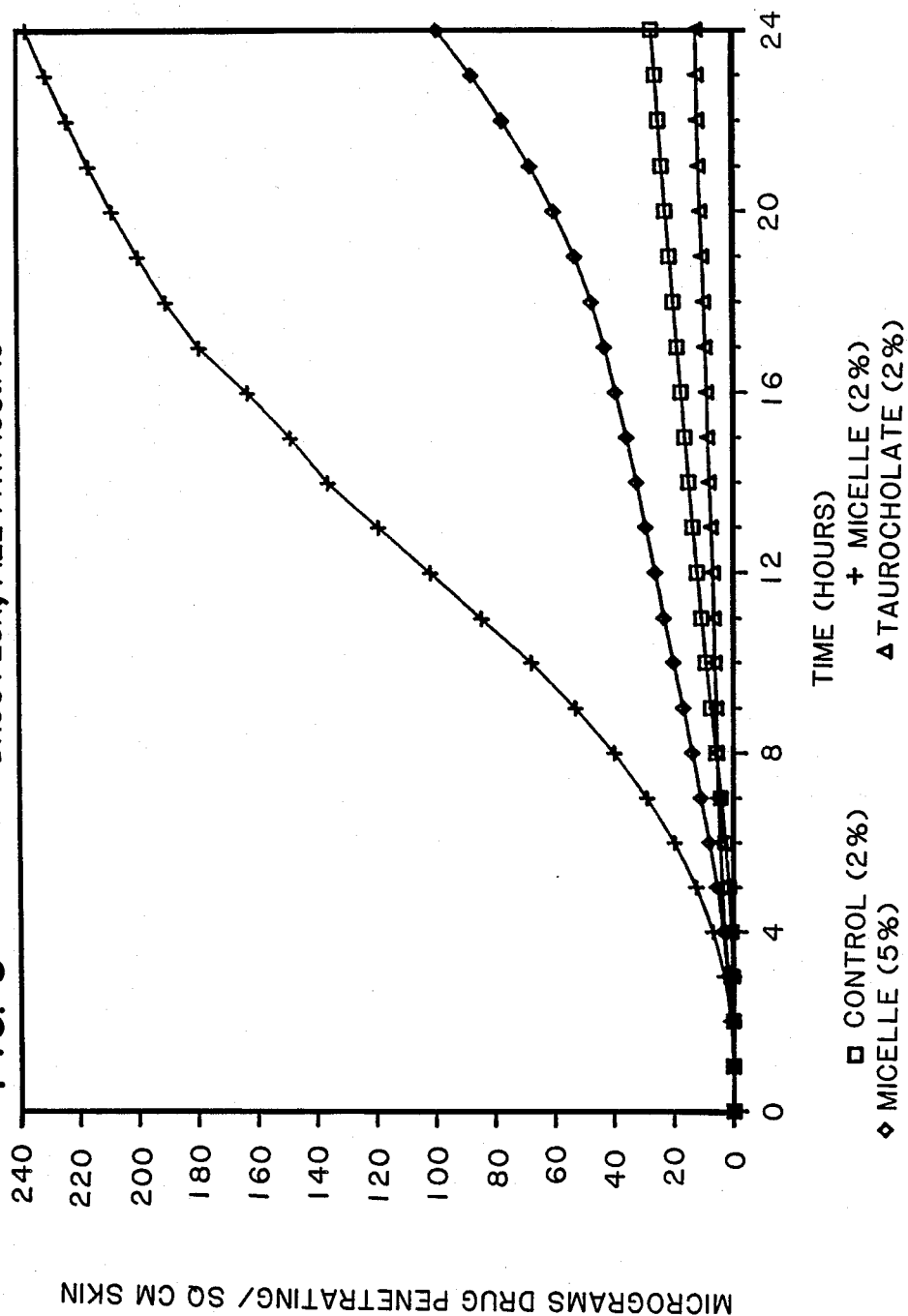
FIG. 5 shows transdermal uptake curves, over a 24 hour period, for control (open squares), 5% minoxidil/sulfosuccinate (open diamonds), 2% minoxidil/sulfosuccinate (crosses), and 2% minoxidil/taurocholate (open triangles) compositions.

The minoxidil composition of the invention is formed by complexing minoxidil with the free acid of an amphipathic compound. The amphipathic compound acts to solubilize minoxidil in both aqueous and lipophilic solvents, and preferred compounds also enhance transdermal uptake of the drug. This section describes amphipathic compounds for use in the invention, and methods of preparing a water-soluble minoxidil composition which is suitable for ointment and cream formulations.

A. Amphipathic Compounds

FIG. 1 shows the molecular structure of minoxidil (1a). The piperidinyl pyrimidinediamine compound is relatively soluble in alcohol, but poorly soluble in water (about 0.2-0.3%), and practically insoluble in chloroform.

The figure also shows the molecular structure of several specific and general types of amphipathic compounds which promote solubilization of the drug in both aqueous and lipophilic solvents and, according to an important feature of the invention, also enhance transdermal uptake of the drug. The amphipathic compounds in this class are characterized by (a) a single lipophilic chain moiety and a polar head group moiety selected from a sulfate, sulfonate, phosphate, or phosphonate free acid, where the pK of the compound is no greater than about 5.0. The exemplary compounds shown in the figure include laureth sulfosuccinate hemiester (1b) and lauryl sulfosuccinate (1c), representative of sulfosuccinate hemiesters, lysophosphatidic acid (1d) and monoalkyl phosphate esters, such as Crodafos TM N3 (1e), monoalkyl phosphonates (1f), monoalkyl sulfate esters, (1g), monoalkl sulfonates (1h), and oleamido-PEG-2-sulfosuccinate (1i), representative of amido-linked amphipaths.

As can be appreciated from the compounds shown in FIG. 1, the lipophilic chain moiety may be a pure hydrocarbon chain, or may contain ether or other chain linkages, such as internal ester or amide linkages. The chains lipophilic chains preferably include at least about 6-8 carbon atoms, and are typically at least about 12 atoms in length. The chains may be attached to the mineral acid head group through ester, ether, thioether, amide, or other stable linkages, as illustrated variously in the FIG. 1 compounds.

A second class of amphipathic compounds which have been examined herein are capable of solubilizing minoxidil in an aqueous medium, but fail to promote transdermal uptake or minoxidil. Several of the compounds in this class are acidic vesicle-forming lipids, typcally having charged phosphate or sulfate free acid head groups, a pK less than about 5, and diacyl, dialkyl or sterol lipophilic moieties. Exemplary compounds include the free acid forms of negatively charged phopholipids, such as phosphatidylglycerol (PG), phosphatidylinositol (PI), and phosphatidic acid (PA), dialkyl phosphate compounds, such as dicetyl phosphate, and sterol mineral acids, such as cholesterol sulfate and taurocholic acid. Other phosphate, phosphonate, sulfate, and sulfonate lipids containing to two or more lipophilic chains or a sterol group through ester, ether, or amide linkages are also in this general class. Representative members of this class are illustrated in FIG. 2. These are: taurocholic acid (2a), cholesterol sulfate (2b), phosphatidic acid (2c), and phosphatidylglycerol (2d).

B. Preparing the Minoxidil Composition

According to an important property of the amphipathic compounds, optimal solubilization of minoxidil by the amphipathic compound occurs at a pH of about 5 or less, where a significant fraction of the compound exists in free acid form. The solubility dependence of minoxidil on pH is illustrated in FIG. 3, for a 20% by weight solution of laureth sulfosuccinate (FIG. 2a compound). Between pH 7.0 and about 5.0, minoxidil solubility increases from about 1.5% to nearly 5%. Little improvement is seen as the pH is lowered beyond about 4.5. For most purposes, a pH of about 5 is preferred, since good solubility is achieved, and skin irritation which may result from below-physiological pH is minimized.

In a preferred method for preparing the composition, a portion of the amphipath is converted to a free acid form, and then "titrated" to the desired pH, e.g., pH 5.0, with the metal salt form of the compound. This approach is illustrated in Example 1, which describes the preparation of a 20 weight % laureth sulfosuccinate solution having a final pH of 5. Here the disodium salt of the compound is converted to the free acid form by passage through a cation exchange resin. Mixing the free acid with the disodium salt, at a ratio of about 1:3, yields a pH 5.0 solution suitable for solubilization of the minoxidil. It is appreciated that the free acid and salt components effectively buffer the solution at the selected pH, obviating the need for additional buffering components.

Alternatively, the compound may be converted to or supplied in free acid form, then adjusted to the selected pH with a suitable base, such as NaOH. Alternatively, the compound may be converted to the free acid form, and complexed directly with minoxidil before increasing the pH, as illustrated in Examples 4–11. Following complex formation, the pH of the composition is then raised, e.g., to pH 5, also as described in Examples 4–11.

Optimal solubilization of the minoxidil in an aqueous formulation requires a molar concentration of amphipathic compound to minoxidil of at least about 1:1, and molar ratios of between 1:1 and 1:5 are typical. FIG. 4 illustrates the increasing solubility of minoxidil with increasing concentration of amphipath in an aqueous solution at pH 5.0. Details are given in Example 4. As seen from the figure, minoxidil solubility up to about 5 percent by weight was achieved at the highest amphipath concentration.

The minoxidil composition is preferably formed by adding dry minoxidil to the aqueous solution of amphipath, prepared as above, to a desired pH and amphipath concentration. Typically, the solution is warmed to about 50° C., and the minoxidil is added slowly with stirring. When the minoxidil is completely dissolved, the solution is cooled and the pH adjusted, if needed. The general method is illustrated in Examples 1 and 2, for the preparation of laureth sulfosuccinate/minoxidil compositions; in Example 5, for the preparation of a Crodafos TM /minoxidil composition; and in Example 6, for the preparation of a taurocholic acid/minoxidil composition. All of the compositions gave clear aqueous solutions.

As indicated above, the composition of the invention includes minoxidil in a substantially non-crystalline or molecular monodisperse or dissolved form. These terms are defined herein to indicate that the minoxidil composition is substantially free of crystalline minoxidil, as judged, for example, by examination by polarization microscopy. It will be appreciated that the minoxidil may be present in a microdispersion, such as in micellar or microemulsion form, and/or or a soluble molecular binary drug/amphipath complex. Thus, in preparing the composition, complete drug solubilization is judged by the absence of the drug in crystalline or microcrystalline form.

The composition may include additional soluble or suspension components, such as metal chelators, preservatives, and/or conventional lipid, emulsifying or gelling agents used in formulating ointment and cream topical formulations. Exemplary metal chelators include EDTA and DTPA, and exemplary preservatives include propyl- and methylparabenparaben. Agents suitable for formulating the composition in cream or ointment form are known.

The use of the aqueous composition for topical administration of minoxidil, and transdermal uptake characteristics of compositions containing each class of amphipathic compound, are considered in Section IV below.

II. Minoxidil Composition in Lipophilic Solvents

According to another important aspect of the invention, the above-described amphipathic compounds which promote solubilization of the drug in aqueous medium, also promote solubilization in lipophilic solvents, such as chloroform, in which the drug is otherwise practically insoluble.

The amphipathic compound used in preparing the minoxidil composition in a lipophilic solvent may be supplied in free form, or converted to a free acid by treatment with a cation-exchange resin, as above. Typically, however, when the compound is supplied in the salt form, the compound is most conveniently converted to a free acid by solvent extraction into the organic solvent phase of an acidified, two-phase extraction mixture, such as in the Bleigh-Dyer extraction procedure detailed in Example 7. In this example, the amphipathic compound is shaken in an acidified chloroform/methanol/water mixture and extracted in free acid form from the lower chloroform phase.

The solution of amphipathic compound containing the free acid form of the compound in a lipophilic solvent (such as the lower-phase extract from a Bleight-Dyer extraction) is mixed with dry minoxidil to form a non-crystalline dispersion of minoxidil in the solvent. For many amphipathic compounds, such as those described in Examples 7–11, dispersion of the drug in a non-flocculated form also requires addition of a vesicle-forming lipid, such as PC, as illustrated in Examples 7–9, or an emulsion-forming agent, such as illustrated in Example 10 and 11. Vesicle- or emulsion-forming lipids are also added to the solution when the composition is to be used in forming a liposomal or emulsion form of molecularly dispersed minoxidil, as detailed in Section III below. Solubilization of minoxidil in the lipophilic solvent containing an amphipathic compound may also be achieved by addition of a co-solvent, such as an alcohol or glycol, to the mixture of minoxidil and amphipath in lipophilic solvent.

One application of the minoxidil/lipophilic solvent mixtures is for delivery of the drug in spray form from a self-propelled atomizer system. Here minoxidil, the amphipathic compound and, if needed, a vesicle- or emulsion-forming agent are co-dissolved in a Freon chlorofluorocarbon solvent. Several fluorochlorocarbon propellant solvents have been used or proposed for self-contained spray devices. Representative solvents includes "Freon 11" ($CCl_3F$), "Freon 12" ($CCl_2F_2$), "Freon 22" ($CHClF_2$), "Freon 113" ($CCl_2FCClF_2$), "Freon 114" ($CClF_2CClF_2$), and "Freon 115" ($CClF_2CF_3$), as well as other fluorochloro substituted methyl and ethyl compounds.

The propellant solution is loaded in a conventional pressurized propellant spray device for delivering a metered amount of spray-dried minoxidil dispersed in the propellant. Since the spray system may require long-term storage of the solution components in the propellant solvent, the lipid components in the system should be selected for stability on storage, for example by employing partially or totally saturated amphipathic and vesicle-forming lipid components.

In use, the propellant spray device produces a fine-particle spray of solubilized minoxidil which is directed against the skin area being treated. The spray particles initially contain minoxidil complexed with the ammphipathic compound and, if present, added co-solubilizing agent, dispersed in the propellant solvent. Rapid evaporation of the solvent, as the spray particles are ejected through the air, yields non-crystalline minoxidil particles which form a layer of drug particles which substantially cover the sprayed skin area.

III. Minoxidil Composition in Lipid Bodies

According to another aspect of the invention, the minoxidil composition can be entrapped in non-crystalline form in both lipid emulsion particles and liposomes, providing additional advantages for topical administration of the drug. One of these advantages, in the case of liposomes, is the ability to modulate the rate of drug release from the composition, by selection of the suitable vesicle-forming lipids. Another is the greater drug loading capacity of lipid particles. Liposomes and emulsion particles are both compatible with topical ointment and cream formulations, and in fact are commonly added to skin creams as moisturizing agents. Liposomes may also be adapted for use with self-propelled spray systems, providing a convenient method of delivery of a non-crystalline, high-concentration minoxidil composition.

Considering first the preparation of non-crystalline minoxidil liposomes, the vesicle forming lipids are preferably neutral phospholipids, such as PC, and may also include negatively charged phospholipids, such as PG, phosphatidylinositol (PI), and phosphatidylserine (PS) which can function as the negatively charged amphipaths in the composition. For the reasons discussed above, however, the amphipathic compound used in the composition is preferably a single chain mineral acid compound of the type which by itself would not form lipid bilayer vesicles upon hydration. Other liposomal lipids, such as cholesterol, may also be included.

Studies conducted in support of the present invention indicate that minoxidil transdermal uptake can be modulated by the factors which affect the fluidity of liposome membranes, such as the extent of phospholipid acyl chain saturation. As a rule, transdermal uptake is is decreased by entrapment of the non-crystalline composition in liposomes. Another factor which is important in rate of drug uptake is the ratio of vesicle-forming lipids to minoxidil. Preferred weight ratios of phospholipid to minoxidil are between about 1:1, which gives relatively high transdermal uptake and 4:1, which gives quite low uptake.

The non-crystalline liposome composition can be formed by a variety of methods which are modifications of existing liposome preparation methods. For example, to prepare the liposomes by lipid hydration, a lipid solution containing minoxidil, the amphipathic compound, and PC, is prepared as above, by dissolving the lipid and minoxidil in the lower-phase solution of amphipath in free acid form. The resulting solution of minoxidil, amphipath, and lipid are dried to a thin film, then hydrated with a suitable aqueous buffer. This hydration method is illustrated in Examples 7-9 below. Alternatively, a film of vesicle-forming lipids alone can be hydrated by a solution of the non-crystalline minoxidil composition, formed as in Section I.

One preferred method of forming the liposome composition uses a novel lipid injection method described in co-owned patent applications for "High-Encapsulation Liposome Processing Method", Ser. No. 908,765, filed Sept. 18, 1986 and now U.S. Pat. No. 4,752,425, and "High-Concentration Liposome Processing Method", Ser. No. 909,122, filed Sept. 18, 1986 and now U.S. Pat. No. 4,781,871. In this method, a solution of minoxidil, amphipathic compound, and vesicle-forming lipids in a preferably chlorofluorocarbon solvent is prepared as described above in Section II. This solution is injected into an aqueous medium under selected temperature and pressure conditions which lead to liposome formation. According to an important feature of the method, solvent injection may be continued, with or without concomitant liposome sizing, until a liposome composition having the consistency of a thick paste is formed. The paste composition has the capability of high minoxidil loading, and also is suitable as a cream or ointment without further processing.

The liposome composition may also be delivered in dried particle form from a self-propelled spray device. Here the liposomes, formed according to above methods, are dried, by spray drying, then suspended in a chlorofluorocarbon propellant solvent. Methods for spray during liposomes and forming stable liposome-particle suspensions in several Freon propellants, have been described in co-owned U.S. patent application for "Liposomes for Inhalation", filed March 6, 1987, Ser. No. 022,937, and similar methods are applicable to the liposomal composition of the present invention. Studies conducted in support of the just-cited patent applications have examined the stability and size characteristics of spray dried liposomes in several Freon propellants. Good liposome stability, as measured by microscopic examination of the liposomes and retention of encapsulated material was seen with Freons 12, 113, 114, and 115.

The suspension of dried minoxidil liposomes in propellant solvent can be administered in metered dose spray form from a conventional pressurized spray device such as used above for delivery of a Freon dispersion solution of minoxidil/amphipath components.

Methods for producing a non-crystalline lipid emulsion composition, according to the invention, may similarly follow standard preparative methods, with modification to include the amphipathic compound needed for minoxidil solubilization. Examples 10 and 11 illustrate methods for forming emulsions of lysoPA/PA and PA alone in a Tween-20 TM emulsion. Briefly, a Bleigh-Dyer solvent extraction containing the free acid form of the lysoPA/PA mixture or PA alone was added to minoxidil, and the lipid solution dried to a thin film. Hydration of the lipid film with an aqueous buffer containing 30% Tween-20 TM yielded an aqueous non-crystalline emulsion.

The emulsion may be formulated in a concentrated, viscous or paste-like form for topical administration, giving the same advantages of high loading available with the liposomal formulation. Alternatively, the emulsion composition can be produced in a self-propelled device by dissolving the mioxidil/amphipath/emulsion lipid components in a Freon solvent, as above, and delivering the components in spray form. Non-crystalline minoxidil/lipid particles are formed during rapid evaporation of the propellant solvent.

IV. Utility

A. Transdermal Uptake Characteristics

The transdermal uptake characteristics of several exemplary minoxidil compositions prepared according to the invention have been examined, as outlined generally in Example 12. Briefly, a small isolated skin patch is sealed between upper and lower chambers of a transdermal cell, and an aliquot of the selected composition (spiked with radiolabeled minoxidil) is applied to the upper surface of the patch. The lower chamber holds a reservoir buffer which is in contact with the lower surface of the skin, and which is circulated through the lower chamber by a constant-rate pump. As drug penetrates the skin patch, it is captured in the lower reservoir, and pumped out of the chamber into assay vials for scintillation counting. Transdermal uptake (drug penetration) is typically measured for over a 24 hour period.

The preparation of the several compositions studies is detailed in Examples 1, 2, and 5–11. The control drug composition used in the studies is a 2% minoxidil composition in an ethanol/propylene glycol/water vehicle. The transdermal uptake of this control formulation, over a 24 hour period, is shown by the open squares in FIG. 5. The cumulative amount of drug taken accross the skin in the 24 hour period is less than about 1% of the total applied to the skin.

Also shown in the figure are the transdermal uptake curves for a soluble 2% minoxidil/laureth sulfosuccinate composition (crosses), and a soluble 5% minoxidil laureth sulfosuccinate composition (open diamonds). As seen, both of the soluble laureth sulfosuccinate compositions gave higher transdermal penetration rates than the control composition, expressed as $\mu g$ drug penetration/$cm^2$ of skin. The total cumulative drug uptake for the 2% composition is about 6% of the total applied to the skin.

Interestingly, the 2% laureth sulfosuccinate composition, which contains about 8% by weight of the laureth sulfosuccinate, gave a significantly higher transdermal uptake than the 5% composition, which contains about 25% by weight of the amphipath. This result may be due to the greater viscosity of the 5% composition, and/or interactions between the surfactant and skin which are less inhibitory in the 2% composition.

FIG. 5 also shows the transdermal uptake for a soluble 2% minoxidil/taurocholic acid composition (open triangles). It is evident that taurocholic acid does not promote the uptake of minoxidil across the skin, even though it is effective in solubilizing the drug in an aqueous formulation.

Figure 6:
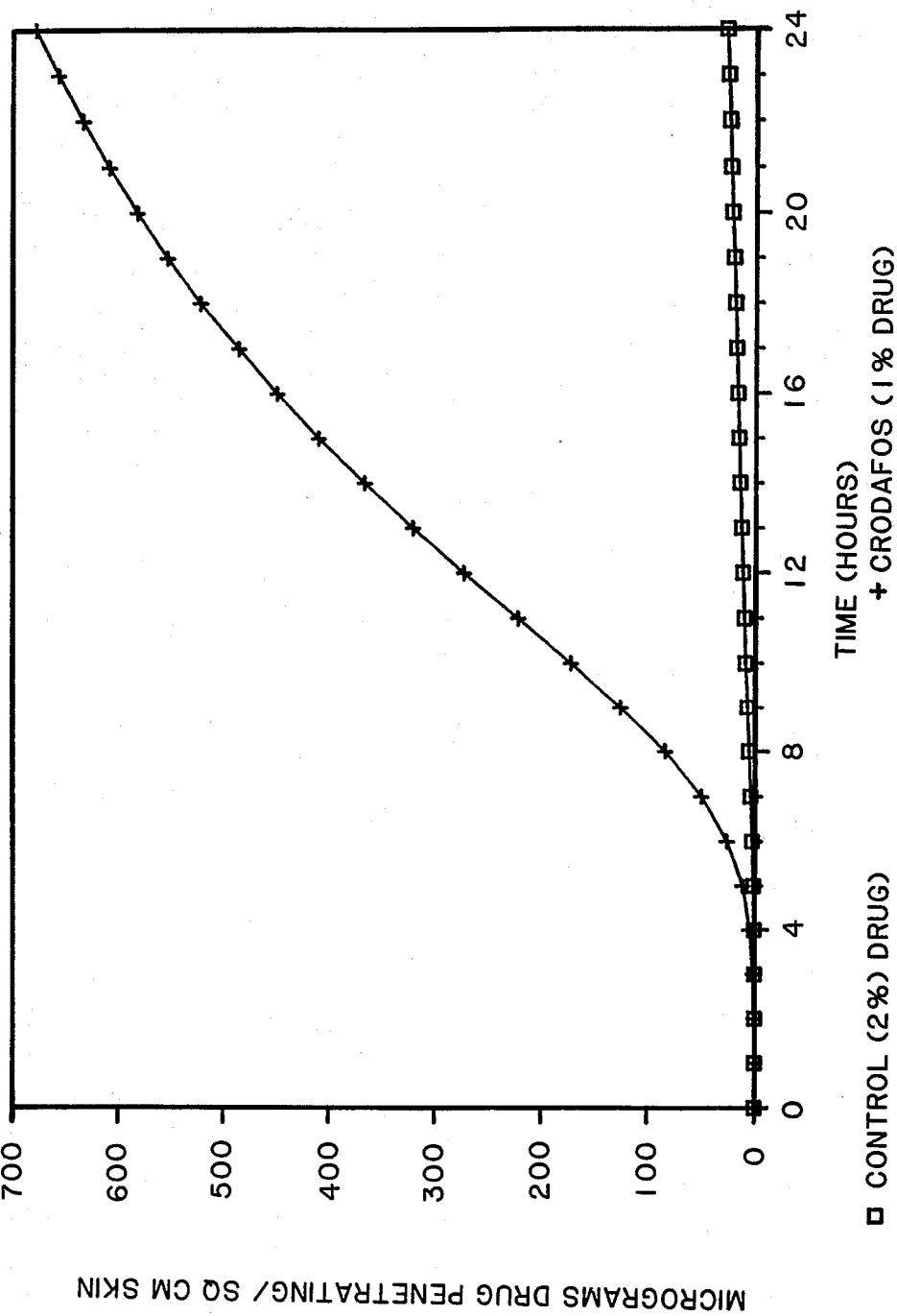
FIG. 6 shows transdermal uptake curves for control (open squares) and a 1% minoxidil/phosphate monoester composition (crosses)

FIG. 6 shows similar transdermal uptake data comparing a minoxidil/CROFADOS composition prepared according to the invention with the above control composition. The transdermal uptake for the composition of about 700 $\mu g/cm^2$ is nearly three time that of the 2% laureth sulfosuccinate composition and about 35 times that of the control material. The total amount of drug material passing through the skin in a 24 hour period is about 35% of the total added.

Figure 7:
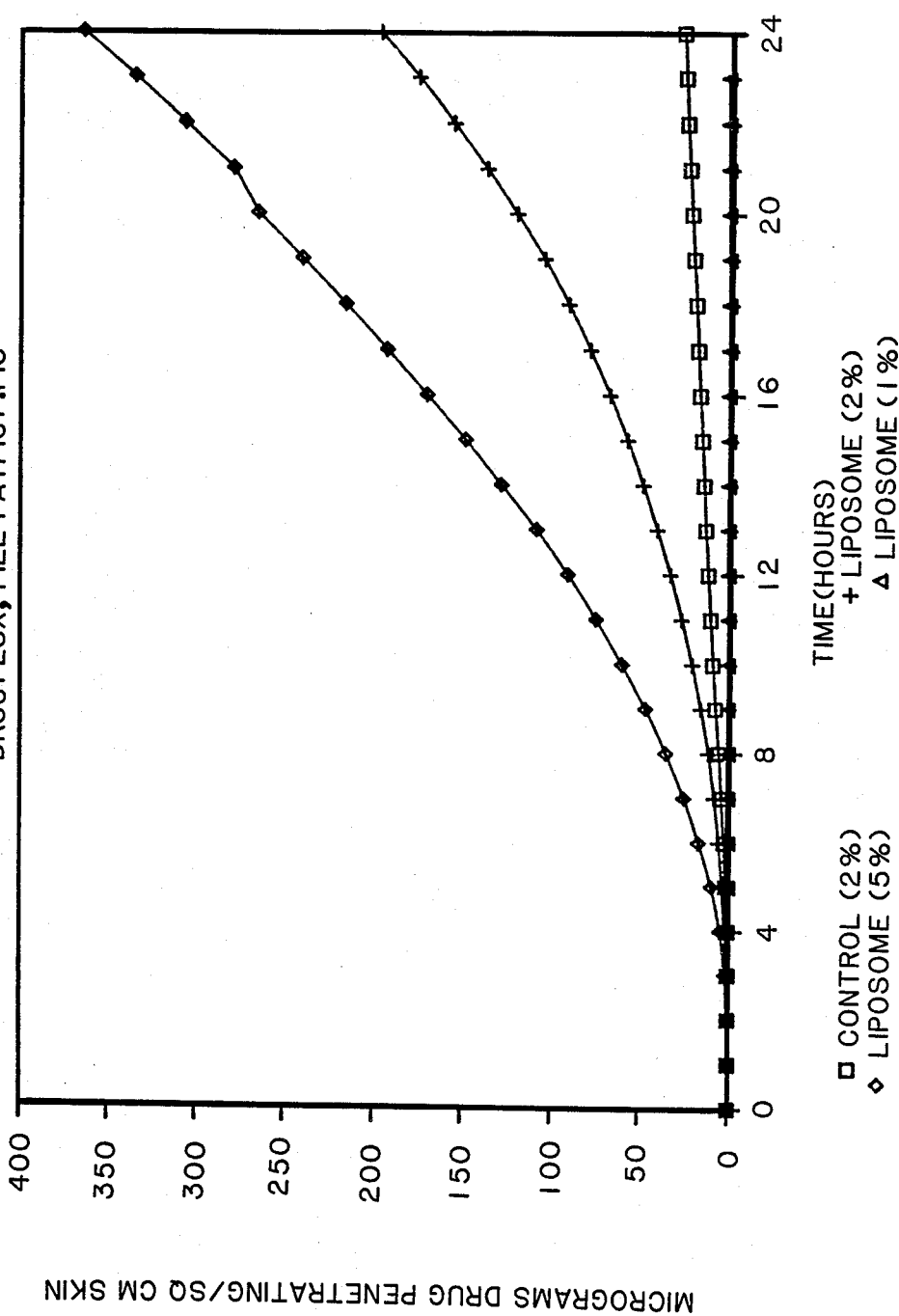
FIG. 7 shows transdermal uptake curves for lauryl sulfosuccinate/PC liposome compositions containing either 2% (crosses) or 5% (open diamonds) minoxidil, a 1% minoxidil/cholesterol sulfate composition (open triangles), and the control composition (open squares)

The transdermal uptake characteristics of several liposomal and emulsion compositions were also examined, and compared with the above minoxidil control composition. FIG. 7 shows transdermal uptake curves for 2% (crosses) and 5% (open diamonds) minoxidil/lauryl sulfosuccinate/PC liposome suspension formed as in Example 7. The data show enhanced transdermal uptake when compared with the control formulation (open squares). It is noted that, in contrast to the results observed for the soluble laureth sulfate composition, the higher percent composition (5% minoxidil) gave greater transdermal uptake. Both liposome formulations gave about 5% total drug penetration over the 24 hour test period. It is also noted that the best liposomal formulation gave higher drug penetration (about 350 $\mu g$ drug/$cm^2$) than the best laureth sulfosuccinate composition (about 240 $\mu g$ drug/$cm^2$).

The figure also shows transdermal uptake for a 1% minoxidil/cholesterol sulfate/PC liposome composition. This composition thus differs from the ones just discussed in that cholesterol sulfate has been substituted for lauryl sulfosuccinate. As seen, virtually no transdermal uptake of minoxidil occurred during the 24 hour test period.

Figure 8:
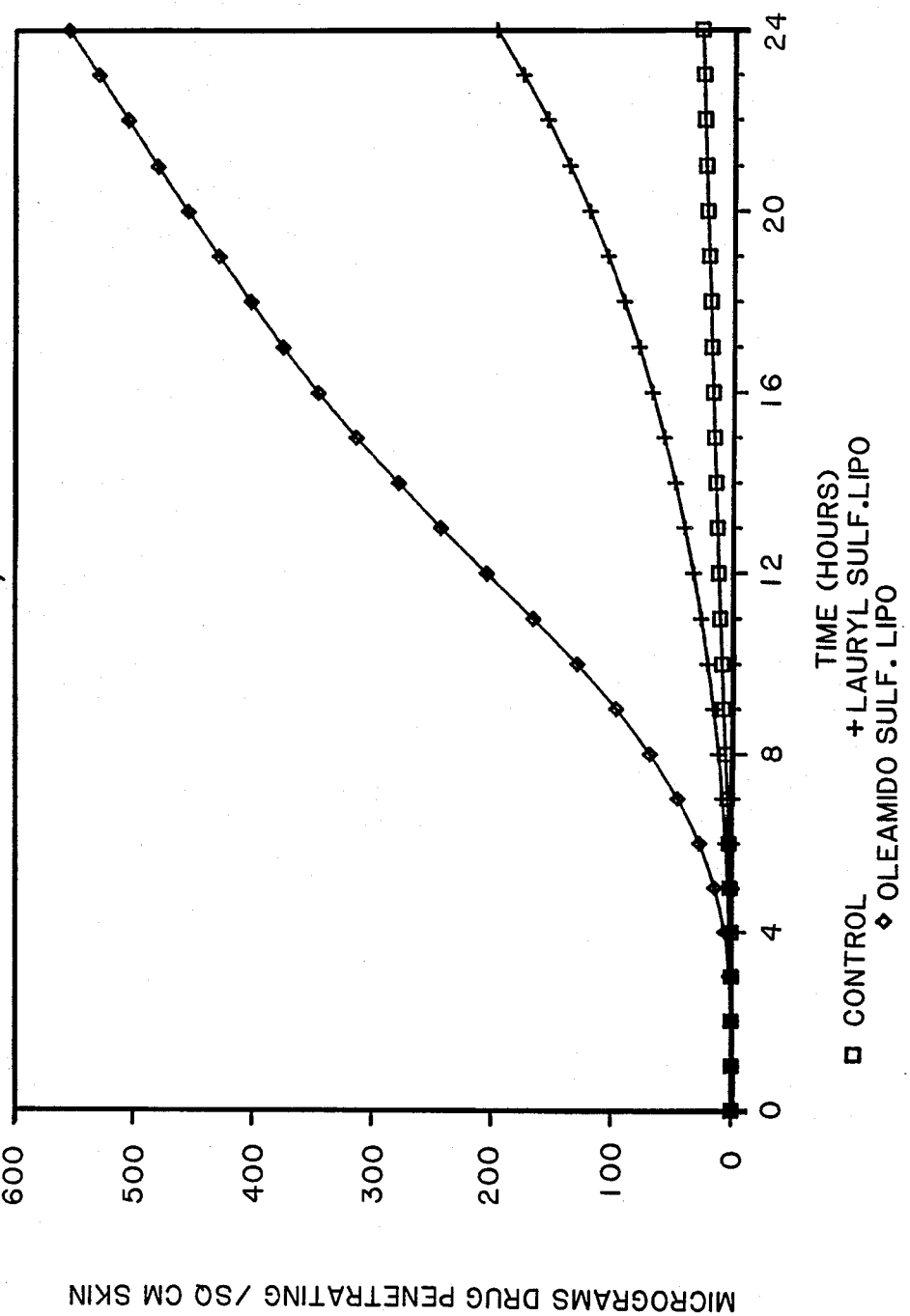
FIG. 8 shows transdermal uptake curves for a 2% minoxidil/oleamido-PEG-2/PC liposome formulation (open diamonds), 2% lauryl sulfosuccinate/PC liposomes (crosses), and the control formulation (open squares)

In FIG. 8, the transdermal uptake of the above 2% minoxidil/lauryl sulfosuccinate/PC liposomes (crosses) is compared with that of 2% minoxidil/oleamido PEG-2 sulfosuccinate/PC liposomes (open diamonds). As observed, the latter composition gave substantially higher transdermal uptake than either 2% or 5% minoxidil/lauryl sulfosuccinate/PC liposome compositions.

Figure 9:
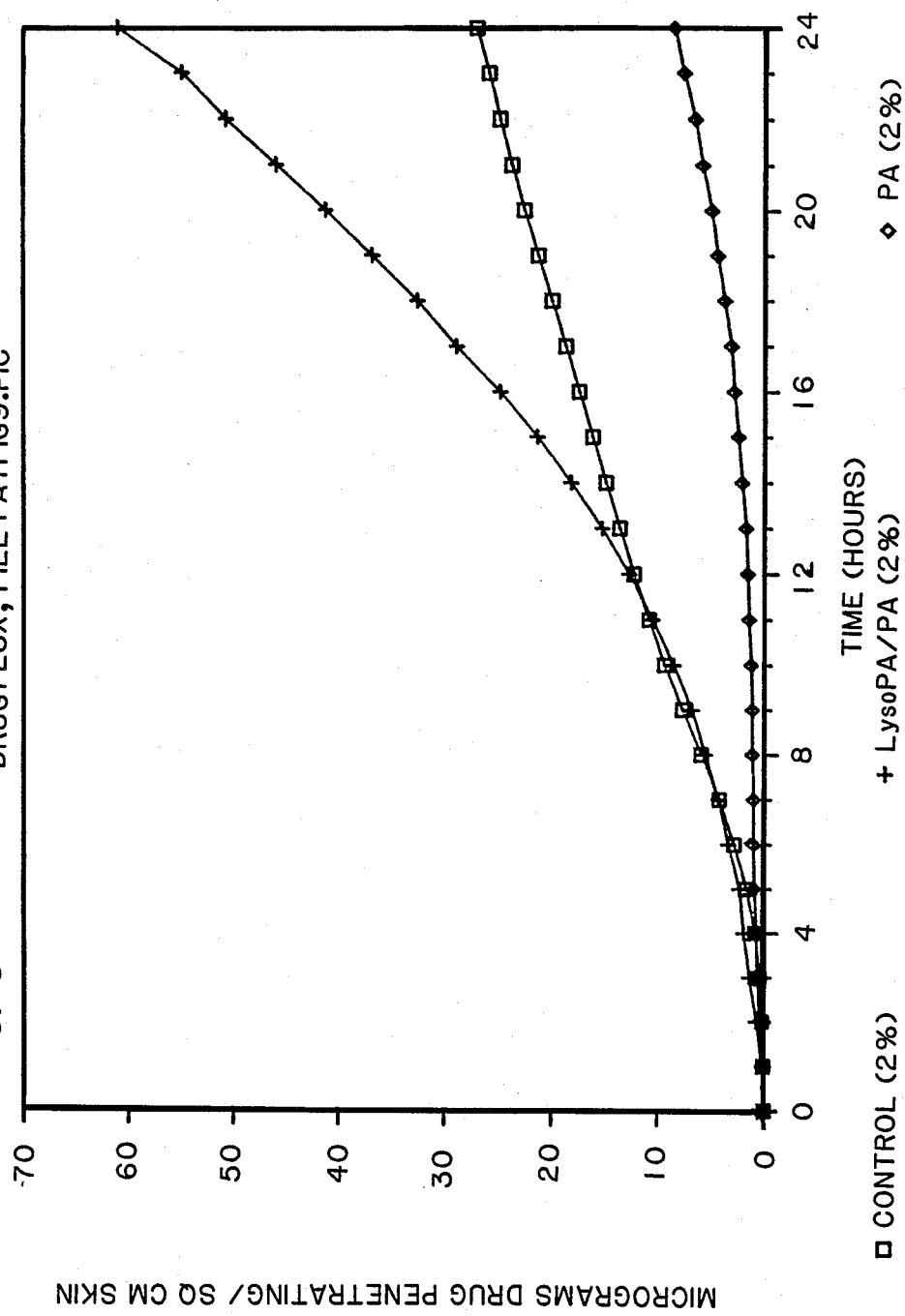
FIG. 9 shows transdermal uptake curves for a 2% minoxidil/lysoPA/PA composition (crosses), a 2% minoxidil/PA composition (open diamonds), and the control formulation (open squares).

Finally in FIG. 9 are shown transdermal uptake curves for suspensions formed from 2% minoxidil and either lysoPA/PA (crosses) or PA alone (open diamonds), according to the preparative methods of Examples 10 and 11, respectively. The control composition is indicated by open squares. PA alone gives very poor drug uptake, whereas with the addition of lysoPA, uptake in enhanced slightly above the control level.

Considering the data as a whole, it is seen that enhanced transdermal uptake is present in each composition where the amphipathic compound used to solubilize minoxidil contains a single lipophilic chain and a sulfosuccinate (sulfate), phosphonate, or phosphate polar head. In all cases where the lipophilic moiety of the amphipath was either a sterol or included more than a single lipophilic chain, transdermal uptake was severely limited.

B. Drug Administration

The composition of the invention may be administered topically in a water-base cream, ointment, or gel form. Several factors contribute to cosmetic advantages of the water-base composition. High drug loading up to 5% or more in non-crystalline form is possible, and the drug remains in a non-crystalline form up to several hours or more after administration, since solvent evaporation is relatively slow and because evaporation can occur without leading to drug crystallization. Since the composition contains little or no alcohol, it can be applied without stinging.

The drug is efficiently taken up by the skin, by virtue of the selected amphipath, and different rates of uptake can be achieved by varying the drug or amphipath concentration, and by selection of different amphipathic compounds.

The water-base composition may additionally contain liposome or lipid-emulsion particles in which the drug can be entrapped in non-crystalline form. In one embodiment, a concentrated liposomal composition having a desired cream or ointment consistency can be formulated using a novel solvent injection system. The liposome formulation can have high loading, and rate of drug uptake can be modulated by choice of lipid components and relative molar amounts of lipid and drug. The lipid formulation is also expected to have the known moisturizing benefits of topical lipid formulations.

In another embodiment, the composition is dispersed in a chlorofluorocarbon solvent for delivery in spray form. The spray form has many advantages of the water-base formulation, including high drug loading and enhanced drug uptake. Additionally, the spray composition has the advantage that it can be applied in a more convenient manner and without matting the hair in the treated scalp region.

The following example illustrate methods of preparing non-crystalline minoxidil compositions according to various embodiments of the invention, and compares transdermal penetration characteristics of the various compositions. The examples are intended to illustrate, but not limit the scope of, the invention.

Materials

Disodium laureth sulfosuccinate was obtained from Sherex (Dublin, CA), and supplied under the trade name Varsulf SBFA-30; disodium lauryl sulfosuccinate, from Mona Industries (Paterson, NJ); disodium salt of taurocholic acid, from Sigma Chemical Co. (St. Louis, MO); oleamido-polyethylene glycol-2 sulfosuccinate, disodium salt, from Mona Industries; Crodafos TM N3 acid (oleth 3 phosphate), from Croda, Inc. (Fullerton, CA); phosphatidic acid (PA), from Avanti Polar Lipids, Inc. (Birmingham, AL); Tween-0 from J. T. Baker (Phillipsburg, NJ); and cholesterol sulfate, from Sigma Chemical Co. (St. Louis, MO). Minoxidil, USP, was obtained from Upjohn (Kalamazoo, MI); methylparaben and propylparaben, from Sigma Chemical Co (St. Louis, MO); diethylenetriaminepentaacetic acid (DTPA), from Aldrich (Milwaukee, WI); and partially hydrogenated egg phosphatidylcholine (PC), from Asahi (Tokyo, Japan). MES (morpholinoethanesulfonic acid) was obtained from Sigma (St. Louis, MO). AG 50W-X8 cation exchange resin were supplied by Bio-Rad (Rockville Center, NY).

Example 1

5% Minoxidil/Laureth Sulfosuccinate Composition

A. Preparing the free acid (laureth sulfosuccinic acid) from disodium laureth sulfosuccinate.

250 ml distilled water was added to 750 ml of a 40% (wt/vol) solution of disodium laureth sulfosuccinate to make one liter of 30% solution. This solution was passed over a prepared column packed with approximately 270 g of AG50W-X8 cation exchange resin that has been converted to the hydrogen ion form. The eluate was collected as a single fraction after the pH of the eluate dropped to 1.3. This eluate was the free acid, lauryl sulfosuccinic acid.

B. Complexing minoxidil with the hemiester sulfosuccinate.

800 ml of the AG50W-X8 eluate from above was mixed with 2,400 ml of a 30% (wt/vol) solution of disodium laureth sulfosuccinate. The resulting solution was heated to about 50° C. and 192 grams minoxidil was added slowly with stirring. After complete dissolution of the minoxidil occurred, the solution was cooled to room temperature, and the pH adjusted to 5.0±0.1. Distilled water sufficient to bring the volume to 3,840 ml was added, yielding a clear, 5% minoxidil/25% surfactant solution which is free of microcrystals, as judged in the polarizing microscope (630×magnification).

The pH of the final dispersion can be varied by changing the ratio of laureth sulfosuccinic acid to disodium laureth sulfosuccinate. A 1:3 ratio (as above after minoxidil dissolution gave a pH of about 4.7±0.2.

Example 2

2% Minoxidil/Laureth Sulfosuccinate Composition

A 2% dispersion of solubilized minoxidil and the free acid of laureth sulfosuccinate was prepared substantially as in Example 1, with the following modifications: The AG50W-X8 column was prepared with 100 g. Two hundred fifty ml of 40% wt/vol disodium laureth sulfosuccinate was diluted to 20% wt/vol surfactant by adding 250 ml distilled water. This solution was passed over the AG50W-X8 cation exchange column and the free acid eluate collector. Four hundred ml of free acid solution was combined with 1,200 ml of 20% disodium laureth sulfosuccinate and 2.0 liters distilled water. The mixture was heated to 50° C. and 80 grams minoxidil was added slowly with mixing. After minoxidil dissolution, other excipients may be added. The mixture was cooled to room temperature, and the pH adjusted to about 5.3±0.1. Distilled water was added to give 4.0 l of a clear dispersion containing 2% solubilized drug and 8% laureth sulfosuccinate.

Example 3

Minoxidil Solubility: pH Dependence

A 20% solution of the free acid of laureth sulfosuccinate in distilled water was prepared as described in Example 1A. More acidic solutions of laureth sulfosuccinate were prepared by increasing the proportion of free acid in the free acid/disodium salt mixture, and more basic forms, by decreasing the ratio. The different-pH solutions were each heated to about 50° C. and dry minoxidil containing tritiated minoxidil was added slowly with stirring until minoxidil saturation was achieved. The dispersions were cooled overnight at 4° C. and centrifuged. The concentration of minoxidil in the clear solution was determined by scintillation counting. The results, expressed in mg mnoxidil/ml laureth sulfosuccinate solution, are plotted in FIG. 3 for two separate experiments. As seen, minoxidil solubility is very low at pH 7.0, and increases linearly to a maximum at a pH about 4.5–5.0.

Example 4

Minoxidil Solubility:

Dependence on Amphipath Concentration

Solutions of the free acid of laureth sulfosuccinate, at concentrations of 0, 5%, 10%, 15%, 20%, and 25% by weight in distilled water were prepared as in Example 1A. Each solution was heated to about 50° C., and radiolabeled minoxidil was added slowly with stirring until minoxidil saturation was achieved, this being monitored as described in Example 3. The pH of each solution was adjusted to about pH 5 prior to centrifugation and scintillation counting. The results, expressed in mg minoxidil/ml laureth sulfosuccinate solution, are plotted in FIG. 4. Minoxidil solubility in the absence of the amphipath is about 3 mg/ml, or 0.3%. With increasing concentrations of the laureth sulfosuccinate, up to 25 weight percent, the solubility of minoxidil increases up to about 50 mg/ml, or 5% at pH 5.

Example 5

Minoxidil/Crodafos TM Composition

Five milliliters of Crodafos TM N3 acid (the oleth-3 phosphate) was obtained in free acid form and diluted in 5 ml distilled water: 10 ml punctilious ethanol. The solution was heated to 37° C., 2 g minoxidil was added slowly with stirring until dissolution. The mixture was diluted with 180 ml of aqueous solution buffered by MES at pH 5.5. Examination of the composition with a polarizing microscope showed no drug crystals in the dispersion containing 1% minoxidil and 5% Crodafos TM N3 acid.

Example 6

Minoxidil/Taurocholic Acid Composition

Taurocholic acid, sodium salt, was converted to a free acid form by the procedure of Example 11. About 100 mg by weight of the free acid form was mixed with 20 mg of dry minoxidil in 1 ml pH 5.5 buffer, yielding a clear solution with a final minoxidil concentration of about 2% by weight. Stirring was continued until a clear solution was obtained, after which the pH of the solution was readjusted to 5.0. No crystals were observed on examination of the composition with a polarizing microscope.

Example 7

Minoxidil/Lauryl Sulfosuccinate/Liposome Composition

This example describes the preparation of a minoxidil/lauryl sulfosuccinate/liposome composition. The free acid form of disodium lauryl sulfosuccinate was formed by the Bleigh-Dyer extraction procedure, as follows: A first solvent mixture was prepared by mixing 8 ml 1 N HCl, 20 ml methanol, and 10 ml chloroform in a 250 ml separatory funnel. To this solvent was added 400 mgs of the disodium lauryl sulfosuccinate, which was dissolved by vigorous shaking. A second solvent mixture containing 7 ml HCl, 10 ml chloroform, and 3 ml distilled water was added to the funnel, which was then shaken vigorously, and allowed to phase separate.

The lower chloroform phase (containing the bulk of the free acid form of the lauryl sulfosuccinate) was collected in a 250 ml round bottom flask containing 580 mgs partially hydrogenated PC (PHPC) and 200 mgs of minoxidil, both in dry form. The flask was swirled until both of the dry components were in solution, and to this solution was added butylated hydroxy toluene (BHT) in chloroform to a final concentration of about 1 mM.

The upper phase in the separatory funnel was reextracted with 5 ml chloroform and 1 ml methanol by vigorous shaking, and the lower phase which formed on standing was collected in the flask containing the minoxidil/lipid solution. The solvent in the flask was removed by rotary evaporation, yielding a thin lipid film. The dried material was further lyophilized for ½ hr to insure complete solvent removal.

The final minoxidil/liposome suspension was formed by hydrating the lipid film with 10 ml of MES buffer, pH 5.5, containing 0.01 % DTPA, using a mechanical "wrist" shaker. Shaking for 1 hour with the flask maintained at 50° C. over a water bath was sufficient to produce complete hydration, as judged by the uniform suspension, which had dropped to about 4 during the hydration step, was raised to 5.0 with 5 N NaOH. Microscopic examination of the liposome suspension showed a heterogeneous-size population of spherical vesicles. No polarizing crystals were noted.

Example 8

Minoxidil/Oleamido Sulfosuccinate/Liposome Composition

Oleamido-(2 polyethylene glycol)-sulfosuccinate was converted to the free acid form by Bleigh-Dyer extraction procedure, substantially as described in Example 7. The first lower chloroform phase was collected in a 250 ml round bottom flask containing 580 mgs partially hydrated PC (PHPC) and 200 mgs of minoxidil, both in dry form. To this was added the second lower extraction phase, as above, and the amphipath/minoxidil/lipid solution was taken to dryness with rotary evaporation and lyophilization.

The final minoxidil/liposome suspension was formed by hydrating the lipid film with 10 ml of MES buffer, pH 5.5, containing 0.01 % DTPA, under hydration conditions used in Example 7. The pH was adjusted to 5.0 after hydration was completed. Microscopic examination of the liposome suspension showed a heterogeneous-size population of spherical vesicles. No polarizing crystals were noted.

Example 9

Minoxidil/Cholesterol Sulfate/Liposome Composition

Cholesterol sulfate was converted to the free acid form by cation exchange chromatography in a methanol/chloroform/water (5:4:1) solvent. The free acid form (120 mgs) was dissolved in 2 ml of chloroform, and this solutions was added to a round bottom flask containing 40 mg minoxidil and 370 mgs of PC. The flask was gently agitated until the components were completely dissolved. The solution was dried to a thin lipid film in a round bottom flask with rotary evaporation and lyophilization, as above. A liposome suspension was prepared as in Example 8. No minoxidil crystal were observed in the suspension.

Example 10

Minoxidil/lipoPA-PA Composition

A mixture of lipophosphatidic acid (lipoPA) and PA was formed by long term storage of pure PA at 4° C. The mixture was confirmed with thin layer chromatography as containing significant portions of both PA and lipoPA (FIG. 2i). One hundred ten mg of the mixture was converted to the free acid form by the Bleigh-Dyer extraction procedure above, and the combined lower-phase extracts were added to a round bottom flask containing 30 mg minoxidil. The flask was gently agitated until the drug was completely dissolved. The solution was dried to a thin lipid film in a round bottom flask with rotary evaporation and lyophilization, as above.

The final minoxidil/lysoPA/PA liposome suspension was formed by hydrating the lipid film with 10 ml of MES buffer, pH 5.5, also containing 30% Tween-0, under hydration conditions used in Example 7. The pH was adjusted to 5.0 after hydration was completed. Microscope examination of the suspension showed a very small (<1 micron diameter) particles. No polarizing crystals were noted.

Example 11

Minoxidil/PA Composition

Freshly obtained PA was examined by thin layer chromatography for purity, and only minor contaminants were observed. One hundred ten milligrams PA was converted to the free acid form by the Bleigh-Dyer extraction procedure above, and the combined lower-phase extracts were added to a round bottom flask containing 30 mg minoxidil. An suspension was formed by hydration of the dried-film lipids, as in Example 9. No minoxidil crystals were observed when examined with polarization microscopy.

Example 12

Transdermal Uptake Studies

A. Experimental protocol

The transdermal cell used for measuring skin penetration has upper and lower chambers which are separated by a skin patch. The lower chamber is designed to permit continuous flow through of saline, which collects drug penetrating from the outer side of the skin (exposed to the upper chamber) through the skin and into the saline in the lower chamber. An infusion pump is used to move through the chamber at a controlled rate (about 5 ml/hour).

Female hairless mice, strain HRS/hr, were obtained from Simonsen (Gilroy, CA). The animals were 7-8 weeks old, and weighed 20-30 gm when used. After sacrifice, three 2 cm diameter skin patches were removed from each animal. The patches were individually mounted in the cell, and held sealed against the lower chamber by an O-ring which is pressed against the patch by clamping.

Prior to adding the drug solution to the skin, a phosphate buffered saline solution was pumped through the system, at a flow rate of about 5 ml/hr for one hour. Fractions were collected continuously from the outlet side of the lower chamber, and dispensed into vials in a fraction collector. Collection time per fraction was one hour. Fractions were collected for up to 24 hours after the drug solution was applied to the skin membrane. After the test period, the skin patch is washed several times, and removed. The hourly fractions, wash fractions obtained at the end of the experiment, and the skin patch itself were counted for radioactivity by conventional scintillation counting methods.

B. Control skin penetration test

The control vehicle was Rogaine TM obtained from Upjohn Co. This formulation contains 2% minoxidil in an ethanol/propylene glycol/water solvent vehicle, and was labeled with tritiated minoxidil before testing. One hundred fifty $\mu$l samples were applied to skin patches and the uptake of minoxidil across the skin monitored as described. Tyical results for a 24 hour test period are shown in FIG. 5, where the control drug data is indicated by the open squares in the figure. As seen, the rate of uptake of the drug in the control formulation is substantially linear over the test period, and reaches a cumulative maximum, at the end of the test period, of about 30 $\mu$g/cm$^2$, corresponding to about 0.5-1.0% of the total drug applied to the skin.

Example 13

Transdermal Penetration: Laureth Sulfosuccinate Compositions

The 5% and 2% minoxidil/lauryl sulfosuccinate compositions prepared as in Examples 1 and 2, respectively, were tested for transdermal uptake, using the experimental methods described in Example 10. Three duplicate runs were made with each of the two formulations, along with the control formulation (Example 12). The results, expressed in terms of cumulative $\mu$g drug uptake/cm$^2$ of skin patch, are shown in FIG. 5, where the data for the 2% composition is indicated by crosses, and for the 5% composition, by open diamonds. The open squares indicate uptake data for the control system, as indicated above.

It is seen that both sulfosuccinate compositions give greater drug transdermal penetration than the control drug formulation. The final cumulative doses correspond to about 0.5-1.0 for control drug, 2% for the 5% composition and 5-6% for the 2% composition.

Example 14

Transdermal Uptake: Crodafos Composition

A 1% minoxidil/Crodafos TM N3 acid was prepared as in Example 5, and tested for transdermal uptake using the experimental methods described in Example 12. These results are from four replicate cells, and are plotted along with the control formulation (Example 12). The results, expressed in $\mu$g drug penetration/cm$^2$ skin, are shown in FIG. 6, where the data for the 1% minoxidil in Crodafos TM N3 acid is indicated by crosses; open squares indicate the control formulation.

Is is seen that the Crodafos TM formulation causes more than an order of magnitude increase in cumulative drug uptake as compared to the control formulation, even though the control formulation has twice the drug loading.

Example 15

Transdermal Uptake: Taurocholic Acid Composition

The 2% minoxidil/taurocholic acid compositions prepared as in Example 6 were tested for transdermal uptake using the experimental method described in Example 12. Four replicate cells were run and the data is plotted in FIG. 5 as open triangles. The open squares indicate transdermal penetration by the control formulation. It can be observed that although taurocholic acid has the same drug loading as the control formulation, less drug is put through the skin.

Example 16

Transdermal Uptake: Lauryl Sulfosuccinate Liposome Composition

The 2% and 5% minoxidil/lauryl sulfosuccinate liposome compositions prepared as in Example 7 were similarly tested for transdermal delivery, with the results therein in FIG. 7. The control formulation is denoted by open squares, the 2% liposome formulation by crosses, and the 5% liposome formulation by open diamonds. The 2% formulation delivers 6 times the cumulative dose of the control formulation at 24 hours, and the 5% formulation delivers 13 times the cumulative dose of the control at 24 hours.

Example 17

Transdermal Uptake:

Oleamido PEG-2 Sulfosuccinate Liposomes

A 2% minoxidil/oleamido PEG-2 sulfosuccinate liposome composition prepared as in Example 8 was tested for transdermal delivery of minoxidil using the experimental protocol described in Example 12. The data are plotted in FIG. 8 as open diamonds, and compared to the control formulation (open squares) and the 2% minoxidil lauryl sulfosuccinate liposomes (crosses).

The oleamido PEG-2 composition produces an approximately threefold increase in transdermal uptake over the lauryl sulfosuccinate liposome preparation. It is evident that changing the hemiester sulfosuccinate in the composition can change the rate of transdermal delivery of drug.

Example 18

Transdermal Uptake: Cholesterol Sulfate Liposome Composition

The minoxidil/cholesterol sulfate/PC composition was prepared as in example 9 and assayed for transdermal drug delivery as in Example 12. The results are plotted as open triangles in FIG. 8. As seen, this composition showed no transdermal penetration, even though the composition was saturated with drug (1% wt/vol).

Example 19

Transdermal Uptake: LysoPA/PA Liposome Composition

The minoxidil/lysoPA/PA in 30% Tween-0 ™ composition prepared as in Example 11 was tested for transdermal drug delivery as in Example 12. The data plotted as crosses in FIG. 9. This composition is similar to the control formulation during the first 12 hours, and then increases substantially relative to the control formulation during the next twelve hour period.

Example 20

Transdermal Uptake: PA Liposome Composition

The minoxidil/PA in Tween-0 composition was prepared as in Example 11, and assayed for transdermal drug penetration as in Example 12. These data are also plotted as open diamonds in FIG. 10. This composition delivers one-third the drug of the control formulation (open squares) and one-sixth that of the composition containing lyso PA (crosses). The results indicate that lyso PA and not PA or Tween-0 ™ is responsible for facilitating transdermal delivery of the drug.

Although the invention has been described with reference to particular methods of preparation, modes of drug administration, and transdermal uptake characteristics, it will be appreciated that various modifications and changes in the methods and results can be made or achieved within the scope of the invention.

It is claimed:

1. A non-crystalline minoxidil composition formed by complexing mnoxidil with the free acid form of an amphipathic compound having a pK less than about 5 and containing a single lipophilic chain moiety and a polar head group selected from the group consisting of a sulfate, sulfonate, phosphate and phosphonate group.

2. The composition of claim 1, wherein the molar ratio of amphipathic compound to minoxidil is at least about 1:1, and the pH is between about 4–6.

3. The composition of claim 1, wherein the amphipathic compound is selected from the group consisting of sulfosuccinic acid hemiesters, alkyl phosphonates, and alkyl phosphate esters.

4. The composition of claim 1, which further includes phospholipids at a phospholipid to minoxidil molar ratio of between about 1:1 and 4:1.

5. The composition of claim 1, wherein the minoxidil and amphipathic compound are dispersed in non-crystalline form in a chlorofluorocarbon solvent.

6. The composition of claim 5, for use in forming a suspension of liposomes containing minoxidil in substantially monomolecular form, which further includes a phospholipid, at a phospholipid to minoxidil molar ratio of between about 1:1 and 4:1, wherein the composition is injected into an aqueous medium under conditions which result in liposome formation in the aqueous medium.

7. The composition of claim 5, for use in delivering minoxidil by means of a self-propelled atomizer device, wherein the composition is contained under pressure in a valved cannister operable to release the composition in spray form.

8. The composition of claim 7 which further includes a phospholipid, at a phospholipid to minoxidil molar ratio of between about 1:1 and 4:1.

9. The composition of claim 1, for use in administering minoxidil topically in ointment form, which further includes at least about 60% by weight of water, and minoxidil is present at a weight concentration of between about 1–5%.

10. The composition of claim 9, which further includes phospholipids, at a phospholipid to minoxidil molar ratio of between about 1:1 and 4:1.

11. A non-crystalline minoxidil composition comprising minoxidil complexed with an ethoxylated sulfosuccininc acid hemiester having a pK less than about 5 and containing a single lipophilic chain moiety.

12. A method of applying minoxidil topically in a non-crystalline form which remains non-crystalline at least several hours after application to the skin, comprising complexing the minoxidil with the free acid form of an amphipathic compound having a pK less than about 5 and containing a single lipophilic chain moiety and a polar head group selected from the group consisting of a sulfate, sulfonate, phosphate and phosphonate group.

13. The method of claim 12, wherein the amphipathic compound is selected from the group consisting of sulfosuccinic acid hemiesters, alkyl phosphonates, and alkyl phosphate esters.

14. The method of claim 12, for use in applying minoxidil in ointment form, which further includes formulating the minoxidil and amphipathic compound in an aqueous medium, to a final minoxidil weight concentration of between 1–5%, and a final weight concentration of water of at least about 60%.

15. The method of claim 14, which further includes adding adding phospholipids to the minoxidil and amphipathic compound, at a phospholipid to minoxidil molar ratio of between about 1:1 and 4:1.

16. The method of claim 12, for use in administering minoxidil in spray form, which further includes dispersing the minoxidil and amphipathic compound in a fluorochlorocarbon solvent, and spraying the resultant mixture from valved cannister containing the mixture under pressure.

17. The method of claim 16, wherein said dispersing includes adding a phospholipid to the mixture, at a phospholipid to minoxidil molar ratio of between about 1:1 and 4:1.

18. A method of producing a topical, non-crystalline minoxidil composition which remains non-crystalline at least several hours after application to skin, comprising complexing the minoxidil with the free acid form of an amphipathic compound having a pK less than about 5 and containing a single lipophilic chain moiety and a polar head group selected from the group consisting of a sulfate, sulfonate, phosphate and phosphonate group.

* * * * *